United States Patent
Pohlers et al.

(10) Patent No.: US 10,527,934 B2
(45) Date of Patent: Jan. 7, 2020

(54) PHOTORESISTS COMPRISING IONIC COMPOUND

(71) Applicant: Rohm and Haas Electronic Materials LLC, Marlborough, MA (US)

(72) Inventors: Gerhard Pohlers, Needham, MA (US); Cong Liu, Shrewsbury, MA (US); Cheng-Bai Xu, Southborough, MA (US); Chunyi Wu, Shrewsbury, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 100 days.

(21) Appl. No.: 13/665,232

(22) Filed: Oct. 31, 2012

(65) Prior Publication Data

US 2014/0120470 A1  May 1, 2014

(51) Int. Cl.
| | |
|---|---|
| G03F 7/004 | (2006.01) |
| C07C 211/63 | (2006.01) |
| C07C 211/64 | (2006.01) |
| G03F 7/20 | (2006.01) |
| G03F 7/039 | (2006.01) |

(52) U.S. Cl.
CPC .......... G03F 7/0045 (2013.01); C07C 211/63 (2013.01); C07C 211/64 (2013.01); G03F 7/0046 (2013.01); G03F 7/0397 (2013.01); G03F 7/20 (2013.01); G03F 7/2041 (2013.01)

(58) Field of Classification Search
CPC ........ G03F 7/0397; G03F 7/0045; G03F 7/20; C07C 211/63; C07C 211/64
USPC ...... 430/270.1, 919, 920; 564/281, 282, 291
See application file for complete search history.

(56) References Cited

U.S. PATENT DOCUMENTS

| | | | |
|---|---|---|---|
| 5,128,232 A | 7/1992 | Thackeray et al. | |
| 5,492,793 A | 2/1996 | Bretya et al. | |
| 5,587,224 A * | 12/1996 | Hsieh | G03G 15/0803 |
| | | | 399/279 |
| 5,843,624 A | 12/1998 | Houlihan et al. | |
| 6,042,997 A | 3/2000 | Barclay et al. | |
| 6,573,024 B2 * | 6/2003 | Chang et al. | 430/270.1 |
| 7,479,361 B2 | 1/2009 | Nagahara et al. | |
| 7,534,554 B2 | 5/2009 | Nagahara et al. | |
| 7,592,126 B2 | 9/2009 | Nishiyama | |
| 8,288,072 B2 * | 10/2012 | Hatakeyama et al. | 430/270.1 |
| 2006/0183218 A1 * | 8/2006 | Takahashi | G03F 7/40 |
| | | | 435/287.8 |
| 2009/0081595 A1 * | 3/2009 | Hatakeyama | G03F 7/0397 |
| | | | 430/323 |
| 2011/0039205 A1 * | 2/2011 | Suzuki | C07D 335/16 |
| | | | 430/270.1 |
| 2011/0183262 A1 * | 7/2011 | Kusaki et al. | 430/270.1 |
| 2011/0223535 A1 | 9/2011 | Liu et al. | |
| 2012/0077120 A1 | 3/2012 | Prokopowicz et al. | |
| 2012/0285929 A1 * | 11/2012 | Matsumura et al. | 216/49 |
| 2013/0004900 A1 * | 1/2013 | Konno et al. | 430/323 |
| 2013/0065180 A1 * | 3/2013 | Kurosawa et al. | 430/270.1 |
| 2013/0143159 A1 * | 6/2013 | Iwashita et al. | 430/285.1 |

FOREIGN PATENT DOCUMENTS

| | | |
|---|---|---|
| EP | 0164248 B1 | 10/1991 |
| EP | 0232972 B1 | 9/1993 |

* cited by examiner

*Primary Examiner* — John S Chu

(74) *Attorney, Agent, or Firm* — Mintz Levin Cohn Ferris Glovsky and Popeo, P.C.; Peter F. Corless

(57) ABSTRACT

New photoresist compositions are provided that comprise a component that comprises a radiation-insensitive ionic compound. Preferred photoresists of the invention may comprise a resin with photoacid-labile groups; a photoacid generator compound; and a radiation-insensitive ionic compound that can function to decrease undesired photogenerated-acid diffusion out of unexposed regions of a photoresist coating layer.

9 Claims, No Drawings

PHOTORESISTS COMPRISING IONIC COMPOUND

1. FIELD

This invention relates to photoresist compositions that comprise an ionic compound with hydrophobic component such as one or more long-chain carbon groups. Preferred photoresists of the invention may comprise a resin with photoacid-labile groups; a photoacid generator and an ionic nitrogen-containing component as disclosed herein that can function to decrease undesired photogenerated-acid diffusion out of unexposed regions of a photoresist coating layer.

2. BACKGROUND

Photoresists are photosensitive films for transfer of images to a substrate. They form negative or positive images. After coating a photoresist on a substrate, the coating is exposed through a patterned photomask to a source of activating energy, such as ultraviolet light, to form a latent image in the photoresist coating. The photomask has areas opaque and transparent to activating radiation that define an image desired to be transferred to the underlying substrate.

Known photoresists can provide features having resolution and size sufficient for many existing commercial applications. However for many other applications, the need exists for new photoresists that can provide highly resolved images of sub-quarter-micron (<0.25 µm) dimension.

Various attempts have been made to alter the make-up of photoresist compositions to improve performance of functional properties. Among other things, a variety of basic compounds have been reported for use in photoresist compositions. See U.S. Pat. Nos. 7,479,361; 7,534,554; and 7,592,126. See also U.S. 2011/0223535 and US 2012/0077120.

SUMMARY

The present invention provides photoresist compositions comprising a resin, a photoacid generator compound (photoacid generator or "PAG"), and an ionic component or compound that comprises one or more long-chain carbon groups. Preferably, such ionic compounds when formulated in a photoresist composition are radiation insensitive, i.e. the ionic compound does not undergo covalent bond cleavage during exposure to radiation (e.g. 193 nm) activating for a photoresist containing the ionic compound as well as any post-exposure thermal treatment.

Preferred ionic compounds can function as a photoacid diffusion control agent during lithographic processing of a photoresist composition coating layer. Such diffusion control may be suitable assessed by improved resolution of a developed relief image of a resist that comprises the ionic basic component relative to the relief image of an otherwise comparable resist that does not contain the ionic component.

Preferred ionic compounds comprise at least one extended carbon-containing moiety, e.g. a straight or branched chain group or cyclic group that comprises 8 or more carbon atoms, preferably 10 or more carbon atoms, still more preferably 12 or more carbon atoms. In many aspects, it will be preferred that an ionic compound comprise at least one substituent having at least 8 carbon or hetero (N, O or S) atoms in a linear chain, even if that linear chain has one or more cyclic or non-cyclic branches or substituents containing additional carbon or hetero atoms.

In certain aspects, the ionic compound may comprise one or more substituents of relatively shorter length, e.g. one or more moieties having 1 to 8 or less carbon atoms, particularly 1 to 6 or less carbon atoms, or 1 to 4 or less carbon atoms or even 1, 2 or 3 carbon atoms.

Photoresists of the invention may be either positive-acting or negative-acting. In a preferred aspect, photoresists of the invention used for short-wavelength imaging applications, such as 193 nm imaging.

Particularly preferred photoresists of the invention may be used in immersion lithography applications.

We have found that use of a present ionic compound in a photoresist composition, including chemically-amplified photoresist compositions, can significantly enhance resolution of a relief image (for example, fine lines) of the resist. In particular, we have found that an ionic compound as disclosed herein can impart significantly enhanced lithographic results, including relative to a comparable photoresist that is otherwise identical to the photoresist that instead contains a distinct basic additive, including non-ionic compounds as well as ionic compounds that do not contain an extended carbon chain substituent. See for instance, the comparative data, which follows.

Methods are also provided for forming relief images of photoresist compositions of the invention (including patterned lines with sub sub-50 nm or sub-20 nm dimensions). Substrates such as a microelectronic wafer also are provided having coated thereon a photoresist composition of the invention. Other aspects are disclosed infra.

DETAILED DESCRIPTION

Without being bound by theory, it is believed that preferred ionic compounds of the invention can function as a surface-active quencher of acid generated during lithographic processing from a resist's photoacid generator component. In particular, in preferred aspects, during lithographic processing, an ionic compound can migrate to the resist-air interface where it can effectively neutralize photogenerated acid in such upper regions of an imaged resist coating layer, thereby resulting in less top erosion. That in turn can result in reduced line edge roughness of the developed resist relief image.

We also have found that preferred ionic compounds as disclosed herein can exhibit reduced volatility relative to non-ionic basic compounds of comparable molecular weight. This can be advantageous and minimize evaporation of the ionic from a resist coating layer during lithographic processing, particularly post-exposure bake steps.

In a preferred aspect, photoresist compositions are provided that comprise (a) one or more resins; (b) one or more acid generators and (c) one or more compounds of the following Formulae (I) and/or (II):

wherein in Formula (I):

$R^1$, $R^2$ and $R^3$ are the same or different non-hydrogen substituents such as optionally substituted alkyl having 1 to 8 carbon atoms or optionally substituted heteroalkyl having 1 to 8 carbon atoms, and preferably one or more of $R^1$, $R^2$ and $R^3$ may have 1, 2, 3 or 4 carbon atoms;

$R^4$ is an optionally substituted alkyl having 1-18, 8-18 or 12-18 or more carbon atoms or heteroalkyl having 1-18 or more carbon atoms;

or two or more of $R^1$, $R^2$, $R^3$ and W are taken together to form a heterocyclic or heteroaromatic ring containing the depicted nitrogen atom ($N^+$), preferably with such heterocyclic or heteroaromatic ring (which may optionally include one or two additional ring heteroatoms selected from O, N, or S) comprising a ring substituent of optionally substituted alkyl having 1-18 or more carbon atoms (e.g., 12-18 carbon atoms) or heteroalkyl having 1-18 or more carbon atoms (e.g., 8-18 or 12-18 carbon atoms);

Y is an organic or inorganic anion;

wherein in Formula (II):

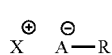

(II)

wherein:

A is an anion moiety such as $SO_3^-$;

R is optionally substituted alkyl (including straight-chain, branched, cyclic, or bridged alkyls) comprising at least 8 (e.g., 8-18) or more carbon atoms or optionally substituted heteroalkyl comprising at least 8 (e.g., 8-18) or more carbon atoms; and X is cation such as a quaternary ammonium cation.

The substituent $R^4$ in Formula (I) and R in Formula (II) suitably may have 8 to 30 or more carbons. In certain preferred aspects, substituent $R^4$ in Formula (I) and R in Formula (II) suitably may contain 10 or more carbon atoms, or 12 or more carbon atoms, e.g., 8-18 or 12-18 carbon atoms. For many resists, substituents $R^4$ in Formula (I) and R in Formula (II) may suitably have 30 or less carbon atoms.

In Formula (I) above, when two or more of $R^1$, $R^2$, $R^3$ and $R^4$ are taken together to form a heterocyclic or heteroaromatic ring containing the depicted nitrogen atom ($N^+$), the formed ring structure suitably may comprise 1 to 3 fused or otherwise covalently-bonded rings, although a heterocyclic or heteroaromatic ring structure that contains a single ring is often preferred. When two or more of $R^1$, $R^2$, $R^3$ and $R^4$ are taken together to form a heterocyclic or heteroaromatic ring containing the depicted nitrogen atom ($N^+$), suitably such heterocyclic or heteroaromatic ring structure may comprise 5 to 24 ring atoms, more typically 5 to 8, 10, 12, 16 or 18 ring atoms, and 1, 2 or 3 hetero (N, O and/or S) ring atoms in addition to the depicted nitrogen atom ($N^+$), more preferably 1 or 2 hetero (N, O and/or S) ring atoms in addition to the depicted nitrogen atom ($N^+$), and in certain aspects even more preferably 1 hetero (N, O and/or S, particularly N) ring atom in addition to the depicted nitrogen atom ($N^+$).

In Formula (I), the anion Y suitably may be organic or inorganic. In certain aspects, an organic counter anion is preferred such as a group comprising a sulfamate moiety or a sulfonate moiety. In certain embodiments of Formula (I), Y comprises a $C_1$-$C_{18}$ alkyl group (including straight-chain, branched, cyclic, or bridged alkyls), or a $C_{12}$-$C_{18}$ alkyl group. In certain embodiments, in a compound of Formula (II), the moiety A-R comprises a sulfamate moiety or a sulfonate moiety. In certain embodiments, the anionic moiety Y (in Formula (I)) or A-R (of Formula (II)) has a pKa of between −2 and 5.

As mentioned, in Formula (I), two or more of $R^1$, $R^2$, $R^3$ and $R^4$ may be taken together to form an alicyclic or aromatic ring containing the depicted nitrogen atom ($N^+$). Suitable ring structures suitably may comprise 5, 6 or more ring members, and preferably such an alicyclic or aromatic ring comprises a ring substituent of optionally substituted alkyl having 8 or more carbon atoms or heteroalkyl having 8 or more carbon atoms. For instance, compounds of Formula (I) that comprise such ring structures include those that correspond to the following Formula (III) or (IV):

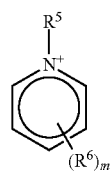

(III)

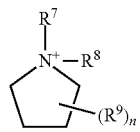

(IV)

wherein in Formula (III), $R^5$ and each $R^6$ are each independently non-hydrogen substituents such as optionally substituted alkyl having 1 to 30 or more carbon atoms or heteroalkyl having 1 to 30 or more carbon atoms, with at least one of $R^5$ and each $R^6$ being optionally substituted alkyl having 1-18 or more carbon atoms (or 8-18 or 12-18 carbon atoms) or heteroalkyl having 1-18 or more carbon atoms (or 8-18 or 12-18 carbon atoms); and m is an integer from 0 (where no $R^6$ groups would be present) to 5, and m is typically 0, 1, 2, 3 or 4; and wherein in Formula (IV), $R^7$, $R^8$ and each $R^9$ are each independently optionally substituted alkyl having 1 to 30 or more carbon atoms (or 8-18 or 12-18 carbon atoms) or heteroalkyl having 1 to 30 or more carbon atoms (or 8-18 or 12-18 carbon atoms), with at least one of $R^7$, $R^8$ and each $R^9$ being optionally substituted alkyl having 1-18 or more carbon atoms (or 8-18 or 12-18 carbon atoms) or heteroalkyl having 1-18 or more carbon atoms (or 8-18 or 12-18 carbon atoms); and n is an integer from 0 (where no $R^9$ groups would be present) to 8, and n is typically 0, 1, 2, 3 or 4.

As stated above, various substituents of the above formulae (i.e. $R^1$, $R^2$, $R^3$ and $R^4$ of Formula (I); R of Formula (II); $R^5$ and $R^6$ of Formula (III); and $R^7$, $R^8$ and $R^9$ or Formula (IV)) may be heteroalkyl. Suitable heteroalkyl groups include alkoxy groups such as moieties having one or more oxygen linkages and from 1 to 8 or more carbon atoms; alkylthio groups such as moieties having one or more thioether linkages and from 1 to 8 or more carbon atom; alkylsulfinyl groups such as moieties having one or more sulfoxide (SO) groups and from 1 to 8 or more carbon atoms; alkylsulfonyl groups such as moieties having from 1 to 8 or more carbon atoms; and aminoalkyl groups such as moieties having one or more primary, secondary and/or tertiary amine groups, and from 1 to 8 or more carbon atoms. Secondary and tertiary amine groups are generally more preferred than primary amine moieties.

As stated, various substituents of the above formulae (i.e. $R^1$, $R^2$, $R^3$ and $R^4$ of Formula (I); R of Formula (II); $R^5$ and $R^6$ of Formula (III); and $R^7$, $R^8$ and $R^9$ or Formula (IV)) may be moieties that are optionally substituted. Substituted moieties are suitably substituted at one or more available positions by e.g. carboxyl (—$CO_2H$), carboxy($C_1$-$C_{30}$)alkyl, ($C_1$-$C_{30}$)alkoxy, sulfonyl, sulfonic acid, sulfonate ester, cyano, halo, and keto. Preferred substituent groups are carboxyl, carboxy($C_1$-$C_{10}$)alkyl, ($C_1$-$C_{10}$)alkoxy, sulfonyl, sulfonic acid, sulfonate ester, cyano, halo, and keto; and more preferably carboxyl, carboxy($C_1$-$C_8$)alkyl, ($C_1$-$C_8$)alkoxy, sulfonyl, sulfonic acid, sulfonate ester, cyano, halo, and keto. Preferred ester groups (carboxyalkyl) are carboxy ($C_1$-$C_6$)alkyl. Preferred alkoxy groups are ($C_1$-$C_6$)alkoxy, and more preferably ($C_1$-$C_5$)alkoxy. By "substituted," it is meant that one or more hydrogens on e.g. a carbon atom of the ionic compound is replaced with one or more of the above substituent groups. A mixture of such substituent groups may be used. The presence of such substituent groups may impart desired solubility to the ionic compound, or may be used to tailor the quenching ability of the ionic compound.

Preferred ionic compounds also may comprise other moieties such as halo (F, Cl, Br, and/or I, particularly F); hydroxyl; cyano, carboxyl (—COOH), ester (e.g. —COOR where R is $C_{1-12}$alkyl). In certain aspects, polar functional groups will be present on an ionic compound in relatively small amounts, e.g., less than 20, 15, 10 or 5 percent of the total molecular weight of an ionic compound will be constituted by polar functional groups of cyano, hydroxyl, carboxy, and/or or ester.

In certain embodiments, an ionic compound (e.g., a compound of Formula (I) or Formula (II)) is a compound having a cationic moiety selected from the group consisting of the following groups:

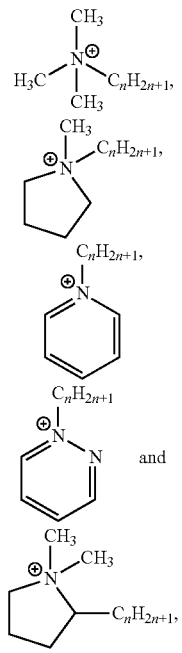

in which n is 12-18;
and an anionic moiety selected from:

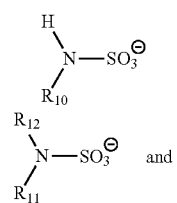

in which:

$R_{10}$ is a linear $C_1$-$C_{18}$ alkyl group (e.g., $C_8$-$C_{18}$ alkyl or $C_{12}$-$C_{18}$ alkyl), or a cyclohexyl, adamantyl, norbornyl, or camphoryl group;

$R_{11}$ and $R_{12}$ are each independently a linear $C_1$-$C_{18}$ alkyl group (e.g., $C_8$-$C_{18}$ alkyl or $C_{12}$-$C_{18}$ alkyl), or a cyclohexyl, adamantyl, norbornyl, or camphoryl group; and $R_{13}$ is a linear $C_1$-$C_{18}$ alkyl group (e.g., $C_8$-$C_{18}$ alkyl or $C_{12}$-$C_{18}$ alkyl), or a cyclohexyl, adamantyl, norbornyl, or camphoryl group.

Preferred ionic compounds of the invention for use in photoresists may be polymeric or non-polymeric, with non-polymeric ionic compounds preferred for many applications. Preferred ionic compounds have relatively low molecular weight, for example, a molecular weight of less than or equal to 3000, more preferably ≤2500, ≤2000, ≤1500, ≤1000, ≤800 or even more preferably ≤500.

Specifically preferred ionic compounds for use in photoresist compositions as disclosed herein include the following:

hexadecyl(tri($C_{1-8}$alkyl)ammonium salt;
hexadecyltrimethylammonium cyclohexylsulfamate (HDTMA-CHSFAM);
tetrabutylammonium cyclohexylsulfamate (TBA-CHS-FAM)
(tetra$C_{1-8}$alkyl)ammonium ($C_{8-30}$alkyl)sulfonate;
tetrabutylammonium 10-camphorsulfonate (TBA-CSA); and
tetrabutylammonium 1-hexadecylsulfonate (TBA-HDSA).

Ionic compounds useful in the present invention are generally commercially available or can be readily synthesized.

Preferably, ionic compounds of the invention are used in positive-acting or negative-acting chemically amplified photoresists, i.e. negative-acting resist compositions which undergo a photoacid-promoted crosslinking reaction to render exposed regions of a coating layer of the resist less developer soluble than unexposed regions, and positive-acting resist compositions which undergo a photoacid-promoted deprotection reaction of acid labile groups of one or more composition components to render exposed regions of a coating layer of the resist more soluble in an aqueous developer than unexposed regions. Ester groups that contain a tertiary non-cyclic alkyl carbon or a tertiary alicyclic carbon covalently linked to the carboxyl oxygen of the ester are generally preferred photoacid-labile groups of resins employed in photoresists of the invention. Acetal groups also are suitable photoacid-labile groups.

Photoresists of the invention typically comprise a resin binder (polymer), a photoactive component such as pone or more photoacid generators, and an ionic compound as disclosed herein. Preferably the resin binder has functional groups that impart alkaline aqueous developability to the photoresist composition. For example, preferred are resin binders that comprise polar functional groups such as hydroxyl or carboxylate. Preferably the resin binder is used in a resist composition in an amount sufficient to render the resist developable with an aqueous alkaline solution.

Preferred imaging wavelengths of the photoresists of the invention include sub-300 nm wavelengths, such as 248 nm, and more preferably sub-200 nm wavelengths, such as 193 nm and EUV.

Particularly preferred photoresists of the invention may be used in immersion lithography applications. See, for example, U.S. Pat. No. 7,968,268 to Rohm and Haas Electronic Materials for a discussion of preferred immersion lithography photoresists and methods. Preferred photoresists for use in immersion application may comprise a resin (which may be fluorinated and/or have photoacid-labile groups) that is separate (not covalently linked) and distinct from a primary resin that has photoacid-labile groups. Thus, the present invention includes in preferred aspects photoresists that comprise: 1) a first resin with photoacid-labile groups; 2) one or more photoacid generator compounds; 3) a second resin that is separate and distinct from the first resin, the second resin may be fluorinated and/or have photoacid-acid groups; and 4) one or more ionic compounds as disclosed herein.

Particularly preferred photoresists of the invention contain an imaging-effective amount of one or more PAGs and one or more ionic compounds as disclosed herein and a resin that is selected from the group of:

1) a phenolic resin that contains acid-labile groups that can provide a chemically amplified positive resist particularly suitable for imaging at 248 nm. Particularly preferred resins of this class include: i) polymers that contain polymerized units of a vinyl phenol and an alkyl (meth)acrylate, where the polymerized alkyl (meth)acrylate units can undergo a deblocking reaction in the presence of photoacid. Exemplary alkyl (meth)acrylates that can undergo a photoacid-induced deblocking reaction include e.g. t-butyl acrylate, t-butyl methacrylate, methyladamantyl acrylate, methyl adamantyl methacrylate, and other non-cyclic alkyl and alicyclic (meth)acrylates that can undergo a photoacid-induced reaction, such as polymers in U.S. Pat. Nos. 6,042,997 and 5,492,793, incorporated herein by reference; ii) polymers that contain polymerized units of a vinyl phenol, an optionally substituted vinyl phenyl (e.g. styrene) that does not contain a hydroxy or carboxy ring substituent, and an alkyl (meth)acrylate such as those deblocking groups described with polymers i) above, such as polymers described in U.S. Pat. No. 6,042,997, incorporated herein by reference; and iii) polymers that contain repeat units that comprise an acetal or ketal moiety that will react with photoacid, and optionally aromatic repeat units such as phenyl or phenolic groups;

2) a resin that is substantially or completely free of phenyl groups that can provide a chemically amplified positive resist particularly suitable for imaging at sub-200 nm wavelengths such as 193 nm. Particularly preferred resins of this class include: i) polymers that contain polymerized units of a non-aromatic cyclic olefin (endocyclic double bond) such as an optionally substituted norbornene, such as polymers described in U.S. Pat. No. 5,843,624; ii) polymers that contain alkyl (meth)acrylate units such as e.g. t-butyl acrylate, t-butyl methacrylate, methyladamantyl acrylate, methyl adamantyl methacrylate, and other non-cyclic alkyl and alicyclic (meth)acrylates; such polymers have been described in U.S. Pat. No. 6,057,083. Polymers of this type may contain in preferred aspects certain aromatic groups such as hydroxynaphthyl.

Preferred resins for use in photoresists to be imaged at sub-200 nm, such as at 193 nm, comprises units of two or more of the following general formulae (I), (II) and (III):

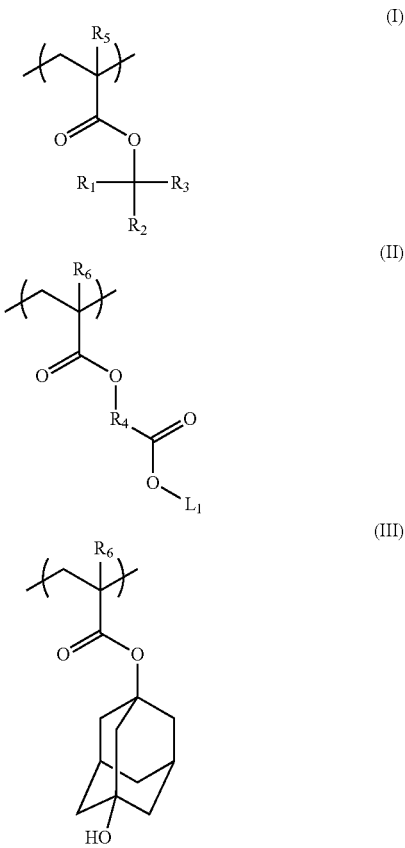

wherein: $R_1$, $R_2$ and $R_3$ are each optionally substituted $(C_1-C_{30})$alkyl group; $R_1$, $R_2$ and $R_3$ may connect to form a ring; $R_4$ is a $(C_1-C_3)$alkylene group; $L_1$ is a lactone group; and $R_5$, $R_6$ and $R_7$ are each hydrogen, fluorine, (C1-C4)alkyl and (C1-C4)fluoroalkyl.

The unit of general formula (I) includes an acid labile group that undergoes a photoacid-promoted deprotection reaction on exposure to activating radiation and heat treatment. This allows for a switch in polarity of the matrix polymer, leading to a change in solubility of the polymer and photoresist composition in an organic developer. Suitable monomers for forming units of formula (I) include, for example, the following:

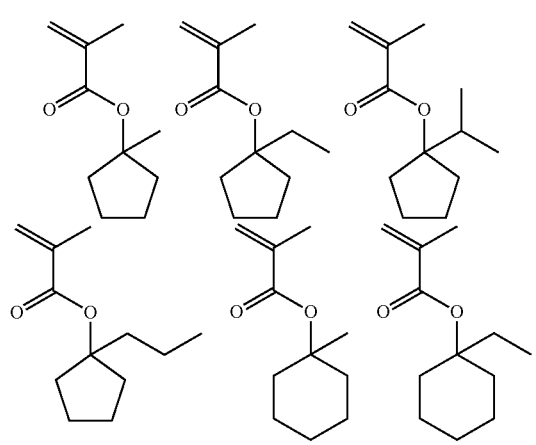

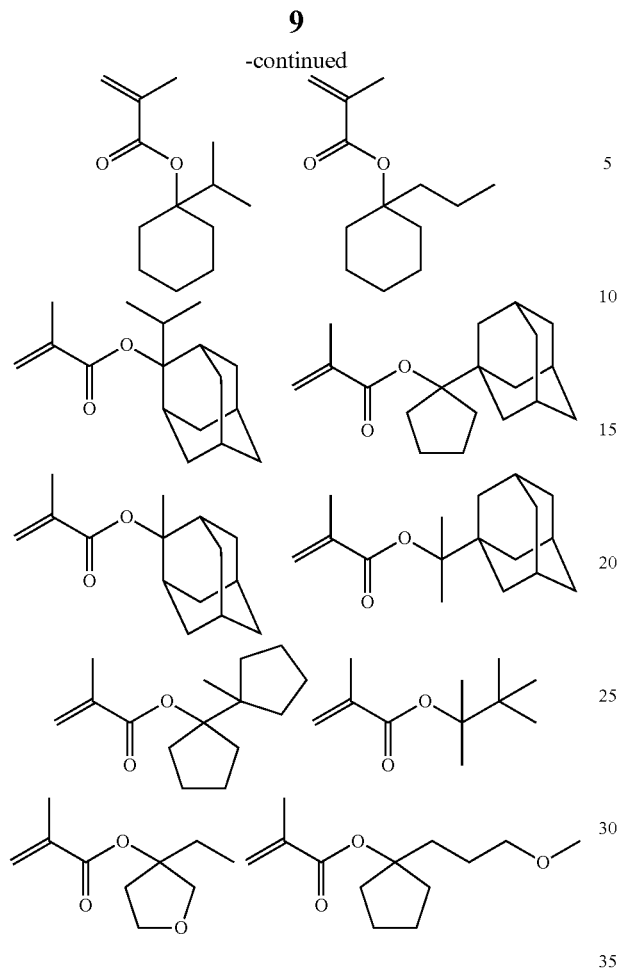
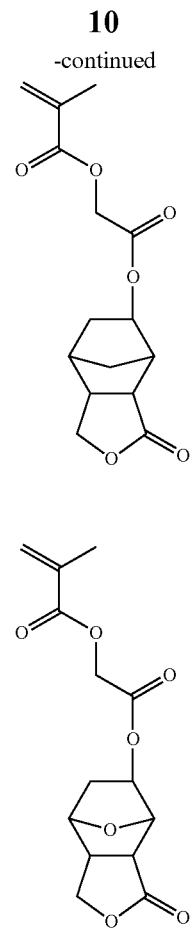
The unit of general formula (II) includes a lactone moiety effective to control the dissolution rate of the matrix polymer and photoresist composition. Suitable monomers for forming units of general formula (II) include, for example, the following:
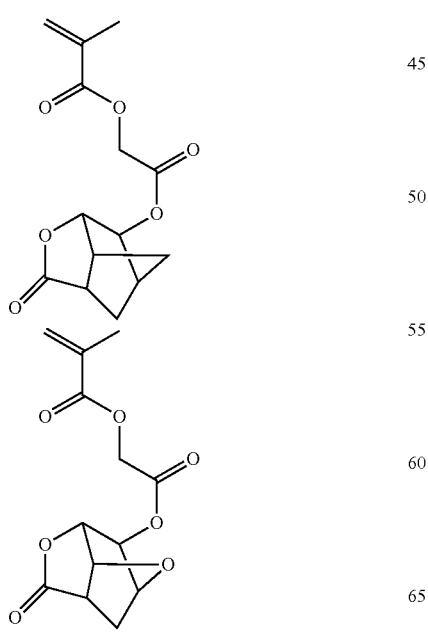
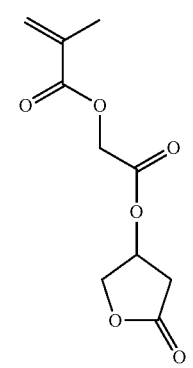
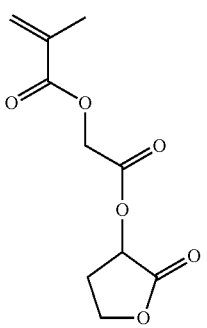

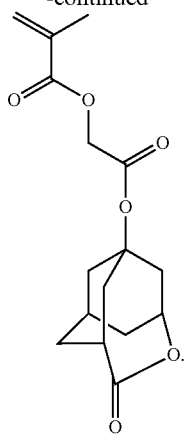

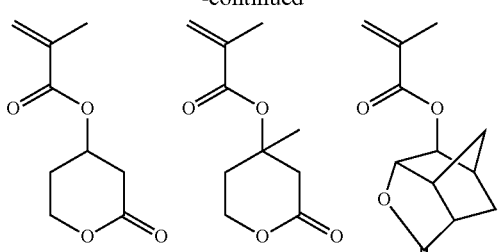

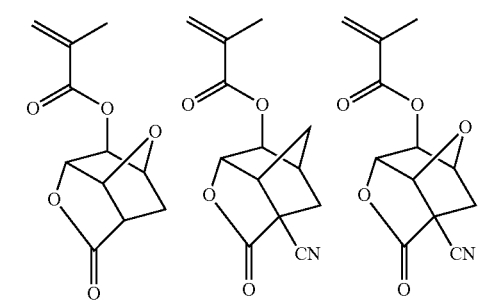

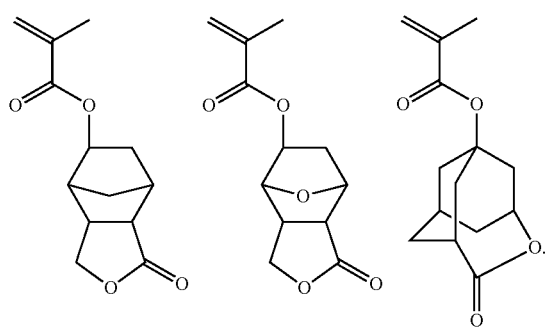

The unit of formula (III) provides a polar group, which enhances etch resistance of the resin and photoresist composition and provides additional means to control the dissolution rate of the resin and photoresist composition. Monomers for forming the unit of formula (III) include 3-hydroxy-1-adamantyl methacrylate (HAMA) and preferably 3-hydroxy-1-adamantyl acrylate (HADA).

The resin can include one or more additional units of general formulae (I), (II) and/or (III) different from the first units. Where additional such units are present in the resin, they will preferably include an additional leaving group-containing unit of formula (I) and/or a lactone-containing unit of formula (II).

In addition to the polymerized units described above, the resin can include one or more additional units which are not of general formula (I), (II) or (III). For example, a particularly suitable lactone group-containing unit is of the following general formula (IV):

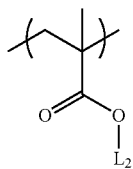

(IV)

wherein: $L_2$ is a lactone group; and the unit of general formula (IV) is different from the unit of general formula (II). The following exemplary monomers are suitable for use in forming the additional lactone unit of general formula (IV):

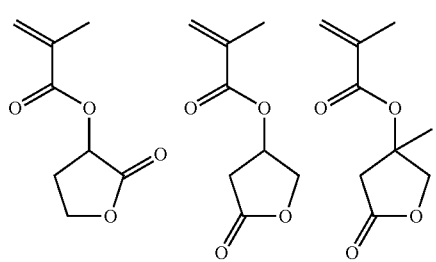

Preferably, $L_1$ in the unit of general formula (II) and $L_2$ in the unit of general formula (IV) are independently chosen from the following lactone groups:

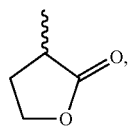

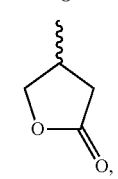

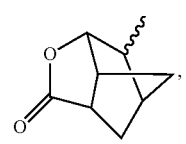

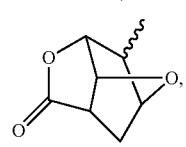

-continued

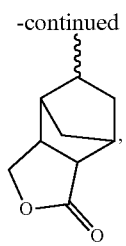,

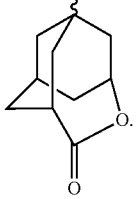 and

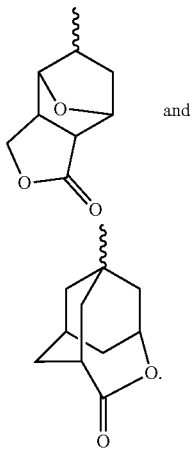

Typically, the additional units for the resin will include the same or similar polymerizable group as those used for the monomers used to form the units of general formula (I), (II) or (III), but may include other, different polymerizable groups in the same polymer backbone, such as those which contain polymerized units of vinyl or a non-aromatic cyclic olefin (endocyclic double bond) such as an optionally substituted norbornene. For imaging at sub-200 nm wavelengths such as 193 nm, the resin is typically substantially free (that is, less than 15 mole %) of phenyl, benzyl or other aromatic groups where such groups are highly absorbing of the radiation. Suitable additional monomeric units for the polymer include, for example, one or more of the following: monomeric units containing ethers, lactones or esters, such as 2-methyl-acrylic acid tetrahydro-furan-3-yl ester, 2-methyl-acrylic acid 2-oxo-tetrahydro-furan-3-yl ester, 2-methyl-acrylic acid 5-oxo-tetrahydro-furan-3-yl ester, 2-methyl-acrylic acid 3-oxo-4,10-dioxa-tricyclo[5.2.1.02,6] dec-8-yl ester, 2-methyl-acrylic acid 3-oxo-4-oxa-tricyclo [5.2.1.02,6]dec-8-yl ester, 2-methyl-acrylic acid 5-oxo-4-oxa-tricyclo[4.2.1.03,7]non-2-yloxycarbonylmethyl ester, acrylic acid 3-oxo-4-oxa-tricyclo[5.2.1.02,6]dec-8-yl ester, 2-methyl-acrylic acid 5-oxo-4-oxa-tricyclo[4.2.1.03,7]non-2-yl ester, and 2-methyl-acrylic acid tetrahydro-furan-3-yl ester; monomeric units having polar groups such as alcohols and fluorinated alcohols, such as 2-methyl-acrylic acid 3-hydroxy-adamantan-1-yl ester, 2-methyl-acrylic acid 2-hydroxy-ethyl ester, 6-vinyl-naphthalen-2-ol, 2-methyl-acrylic acid 3,5-dihydroxy-adamantan-1-yl ester, 2-methyl-acrylic acid 6-(3,3,3-trifluoro-2-hydroxy-2-trifluoromethyl-propyl)-bicyclo[2.2.1]hept-2-yl, and 2-bicyclo[2.2.1]hept-5-en-2-ylmethyl-1,1,1,3,3,3-hexafluoro-propan-2-ol; monomeric units having acid labile moieties, for example, ester groups that contain a tertiary non-cyclic alkyl carbon such as t-butyl, or a tertiary alicyclic carbon such as methyladamantyl or ethylfenchyl covalently linked to a carboxyl oxygen of an ester of the polymer, 2-methyl-acrylic acid 2-(1-ethoxy-ethoxy)-ethyl ester, 2-methyl-acrylic acid 2-ethoxymethoxy-ethyl ester, 2-methyl-acrylic acid 2-methoxymethoxy-ethyl ester, 2-(1-ethoxy-ethoxy)-6-vinyl-naphthalene, 2-ethoxymethoxy-6-vinyl-naphthalene, and 2-methoxymethoxy-6-vinyl-naphthalene. The additional units if used are typically present in the polymer in an amount of from 10 to 30 mol %.

Exemplary preferred resins include, for example, the following:

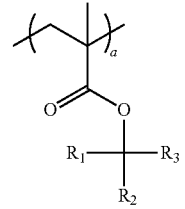

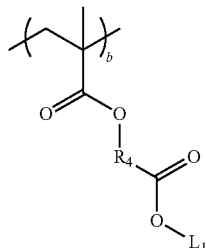

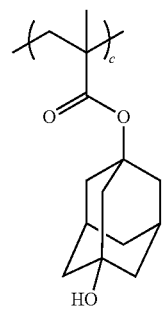

wherein: $0.3 < a < 0.7$; $0.3 < b < 0.6$; and $0.1 < c < 0.3$;

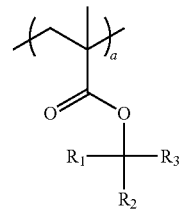

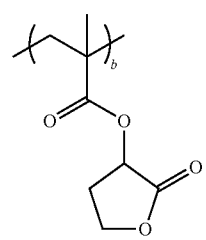

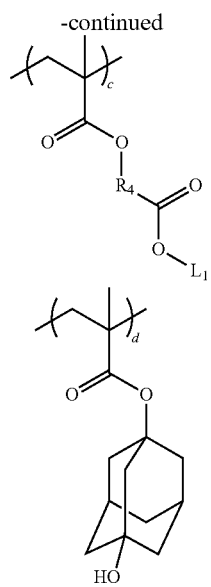

wherein: 0.3<a<0.7; 0.1<b<0.4; 0.1<c<0.4, and 0.1<d<0.3;

Blends of two or more resins can be used in the compositions of the invention. The resin is present in the resist composition in an amount sufficient to obtain a uniform coating of desired thickness. Typically, the resin is present in the composition in an amount of from 70 to 95 wt % based on total solids of the photoresist composition. Because of improved dissolution properties of the resin in organic developers, useful molecular weights for the resin are not limited to lower values, but cover a very broad range. For example, the weight average molecular weight $M_w$ of the polymers is typically less than 100,000, for example, from 5000 to 50,000, more typically from 6000 to 30,000 or from 7,000 to 25,000.

Suitable monomers used in forming the resins are commercially available and/or can be synthesized using known methods. The resins can readily be synthesized by persons skilled in the art using the monomers with known methods and other commercially available starting materials.

Photoresists of the invention also may comprise a single PAG or a mixture of distinct PAGs, typically a mixture of 2 or 3 different PAGs, more typically a mixture that consists of a total of 2 distinct PAGs. The photoresist composition comprises a photoacid generator (PAG) employed in an amount sufficient to generate a latent image in a coating layer of the composition upon exposure to activating radiation. For example, the photoacid generator will suitably be present in an amount of from 1 to 20 wt % based on total solids of the photoresist composition. Typically, lesser amounts of the PAG will be suitable for chemically amplified resists as compared with non-chemically amplified materials.

Suitable PAGs are known in the art of chemically amplified photoresists and include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; nitrobenzyl derivatives, for example, 2-nitrobenzyl-p-toluenesulfonate, 2,6-dinitrobenzyl-p-toluenesulfonate, and 2,4-dinitrobenzyl-p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenesulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine.

Photoresists of the invention comprise one or more ionic compounds as disclosed herein in a wide amount range, such as from 0.005 to 15 wt %, based on the weight of the PAG, preferably from 0.01 to 15 wt %, and even more preferably from 0.01 to 10 wt %. The added ionic compound is suitably used in amounts of 0.01, 0.05, 0.1, 0.02, 0.3, 0.4, 0.5 or 1 to 10 or 15 wt % relative to the PAG, and more typically amounts of 0.01, 0.05, 0.1, 0.02, 0.3, 0.4, 0.5 or 1 to 5, 6, 7, 8, 9 or 10 weight percent.

The present photoresist compositions typically comprise a solvent. Suitable solvents include, for example: glycol ethers such as 2-methoxyethyl ether (diglyme), ethylene glycol monomethyl ether, and propylene glycol monomethyl ether; propylene glycol monomethyl ether acetate; lactates such as methyl lactate and ethyl lactate; propionates such as methyl propionate, ethyl propionate, ethyl ethoxy propionate and methyl-2-hydroxy isobutyrate; Cellosolve esters such as methyl Cellosolve acetate; aromatic hydrocarbons such as toluene and xylene; and ketones such as acetone, methylethyl ketone, cyclohexanone and 2-heptanone. A blend of solvents such as a blend of two, three or more of the solvents described above also are suitable. The solvent is typically present in the composition in an amount of from 90 to 99 wt %, more typically from 95 to 98 wt %, based on the total weight of the photoresist composition.

The photoresist compositions can also include other optional materials. For example, the compositions can include one or more of actinic and contrast dyes, anti-striation agents, plasticizers, speed enhancers, sensitizers, and the like. Such optional additives if used are typically present in the composition in minor amounts such as from 0.1 to 10 wt % based on total solids of the photoresist composition.

The photoresists of the invention are generally prepared following known procedures. For example, a photoresist composition of the invention can be prepared by dissolving the components of the photoresist in a suitable solvent. The resin binder component of photoresists resists of the invention are typically used in an amount sufficient to render an exposed coating layer of the resist developable such as with an aqueous alkaline solution. More particularly, a resin binder will suitably comprise 50 to 90 weight percent of total solids of the resist. The photoactive component should be present in an amount sufficient to enable generation of a latent image in a coating layer of the resist. More specifically, the photoactive component will suitably be present in an amount of from 1 to 40 weight percent of total solids of a photoresist. Typically, lesser amounts of the photoactive component will be suitable for chemically amplified resists.

The desired total solids content of the present photoresist compositions will depend on factors such as the particular polymers in the composition, final layer thickness and exposure wavelength. Typically the solids content of the photoresist varies from 1 to 10 wt %, more typically from 2 to 5 wt %, based on the total weight of the photoresist composition.

Preferred negative-acting compositions of the invention comprise a mixture of materials that will cure, crosslink or harden upon exposure to acid, and a photoactive component of the invention. Particularly preferred negative acting compositions comprise a resin binder such as a phenolic resin, a crosslinker component and a photoactive component of the invention. Such compositions and the use thereof has been disclosed in European Patent Applications 0164248 and 0232972 and in U.S. Pat. No. 5,128,232 to Thackeray et al. Preferred phenolic resins for use as the resin binder component include novolaks and poly(vinylphenol)s such as those discussed above. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by American Cyanamid under the trade names Cymel 300, 301 and 303. Glycoluril resins are sold by American Cyanamid under trade names Cymel 1170, 1171, 1172, urea-based resins are sold under the trade names of Beetle 60, 65 and 80, and benzoguanamine resins are sold under the trade names Cymel 1123 and 1125.

The photoresists of the invention can be used in accordance with known procedures. Though the photoresists of the invention may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and nonexposed regions of the resist coating layer, and then developed preferably with an aqueous alkaline developer to form a relief image. The substrate on which a resist of the invention is applied and processed suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Substrates used for liquid crystal display and other flat panel display applications are also suitably employed, for example, glass substrates, indium tin oxide coated substrates and the like. A liquid coating resist composition may be applied by any standard means such as spinning, dipping or roller coating.

The exposure energy should be sufficient to effectively activate the photoactive component of the radiation sensitive system to produce a patterned image in the resist coating layer. Suitable exposure energies typically range from 1 to 300 mJ/cm$^2$. As discussed above, preferred exposure wavelengths include sub-200 nm such as 193 nm.

The photoresist layer (with overcoated barrier composition layer, if present) may be preferably exposed in an immersion lithography system, i.e. where the space between the exposure tool (particularly the projection lens) and the photoresist coated substrate is occupied by an immersion fluid, such as water or water mixed with one or more additives such as cesium sulfate which can provide a fluid of enhanced refractive index. Preferably the immersion fluid (for example, water) has been treated to avoid bubbles, for example water can be degassed to avoid nanobubbles.

References herein to "immersion exposing" or other similar term indicates that exposure is conducted with such a fluid layer (for example, water or water with additives) interposed between an exposure tool and the coated photoresist composition layer.

After exposure, a thermal treatment is typically employed for chemically-amplified photoresists. Suitable post-exposure bake temperatures are from about 50° C. or greater, more specifically from 50 to 140° C. For an acid-hardening negative-acting resist, a post-development bake may be employed if desired at temperatures of from 100 to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

The invention also provide methods for forming relief images of the photoresists of the invention, including methods for forming highly resolved patterned photoresist images (for example, a patterned line having essentially vertical sidewalls) of sub-quarter μm dimensions or less, such as sub-0.2 or sub-0.1 μm dimensions.

The invention further provides articles of manufacture comprising substrates such as a microelectronic wafer or a flat panel display substrate having coated thereon the photoresists and relief images of the invention.

EXAMPLES 1-5: PREPARATION OF PHOTORESIST COMPOSITIONS

Example 1: Preparation of Photoresist Composition (Resist A)

A positive chemically amplified photoresist composition (referred to herein as Resist A) was prepared by combining 2.148 g Polymer A (Polymer A has a Mw=6K and was prepared by using reaction of immediately below depicted monomers M1, M2 and M3 in a molar feed ratio of M1/M2/M3=4/4/2).

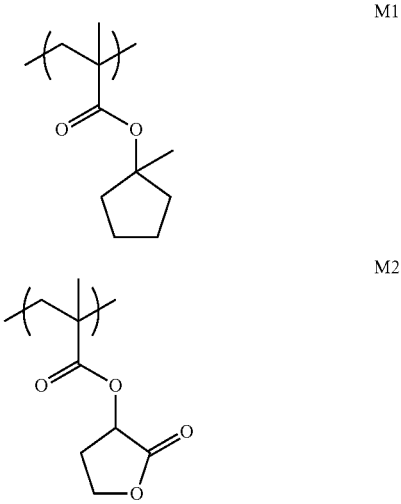

-continued

M3

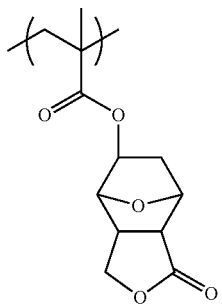

0.364 g of photoacid generator Triphenylsulfonium 1,1-difluoro-2-(((1r,3s,5R,7S)-3-hydroxyadamantan-1-yl)methoxy)-2-oxoethanesulfonate (TPS-ADOH-CDFMS), 0.08 g of surface active ionic quencher hexadecyltrimethylammonium cyclohexylsulfamate (HDTMA-CHSFAM), 0.108 g of a second Polymer B (Polymer B was prepared by using reaction of the immediately below monomers M1 and M2 in a molar feed ratio M1/M2=6/94),

M1

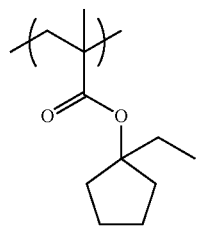

M2

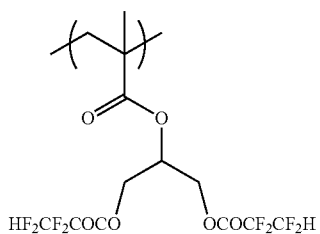

19.46 g propylene glycol methyl ether acetate, 63.245 g methyl-2-hydroxy-iso-butyrate and 14.595 g of cyclohexanone.

Example 2: Preparation of Photoresist Composition (Resist B (Comparative))

A positive chemically amplified photoresist composition (referred to herein as Resist B (a comparative resist) was prepared by combining 2.156 g Polymer A (Polymer A as described in Example 1 above, M1/M2/M3=4/4/2 mole ratio, Mw=6K), 0.364 g of photoacid generator Triphenylsulfonium 1,1-difluoro-2-(((1r,3s,5R,7S)-3-hydroxyadamantan-1-yl)methoxy)-2-oxoethanesulfonate (TPS-ADOH-CDFMS), 0.072 g of ionic quencher tetrabutylammonium cyclohexylsulfamate (TBA-CHSFAM), 0.108 g of Polymer B (Polymer B as described in Example 1 above, M1/M2=6/94 mole ratio), 19.46 g propylene glycol methyl ether acetate, 63.245 g methyl-2-hydroxy-iso-butyrate and 14.595 g of cyclohexanone.

Example 3: Preparation of Photoresist Composition (Resist C)

A positive chemically amplified photoresist composition (referred to herein as Resist C) was prepared by combining 2.134 g Polymer A (Polymer A as described in Example 1 above, M1/M2/M3=4/4/2 mole ratio, Mw=6K), 0.364 g of photoacid generator Triphenylsulfonium 1,1-difluoro-2-(((1r,3s,5R,7S)-3-hydroxyadamantan-1-yl)methoxy)-2-oxoethanesulfonate (TPS-ADOH-CDFMS), 0.094 g of surface active ionic quencher tetrabutylammonium 1-hexadecylsulfonate (TBA-HDSA), 0.108 g of Polymer B (Polymer B as described in Example 1 above, M1/M2=6/94 mole ratio), 19.46 g propylene glycol methyl ether acetate, 63.245 g methyl-2-hydroxy-iso-butyrate and 14.595 g of cyclohexanone.

Example 4: Preparation of Photoresist Composition (Resist D (Comparative))

A positive chemically amplified photoresist composition (referred to herein as Resist D (a comparative resist) was prepared by combining 2.146 g Polymer A (Polymer A as described in Example 1 above, M1/M2/M3=4/4/2 mole ratio, Mw=6K), 0.364 g of photoacid generator Triphenylsulfonium 1,1-difluoro-2-(((1r,3s,5R,7S)-3-hydroxyadamantan-1-yl)methoxy)-2-oxoethanesulfonate (TPS-ADOH-CDFMS), 0.082 g of ionic quencher tetrabutylammonium 10-camphorsulfonate (TBA-CSA), 0.108 g of Polymer B (Polymer B as described in Example 1 above, M1/M2=6/94 mole ratio), 19.46 g propylene glycol methyl ether acetate, 63.245 g methyl-2-hydroxy-iso-butyrate and 14.595 g of cyclohexanone.

Example 5: Preparation of Photoresist Composition (Control)

A positive chemically amplified photoresist composition (referred to herein as control photoresist) was prepared by combining 2.19 g Polymer A (Polymer A as described in Example 1 above, M1/M2/M3=4/4/2 mole ratio, Mw=6K), 0.364 g of photoacid generator Triphenylsulfonium 1,1-difluoro-2-(((1r,3s,5R,7S)-3-hydroxyadamantan-1-yl)methoxy)-2-oxoethanesulfonate (TPS-ADOH-CDFMS), 0.038 g of quencher trihydroxymethyl-carbamic acid tert-butyl ester, 0.108 g of Polymer B (Polymer B as described in Example 1 above, M1/M2=6/94 mole ratio), 19.46 g propylene glycol methyl ether acetate, 63.245 g methyl-2-hydroxy-iso-butyrate and 14.595 g of cyclohexanone.

Example 6: Lithographic Processing of Photoresists

Each of the photoresists of the above Examples 1 through 5 separately spin coated on organic bottom antireflective coating (BARC AR104 40 nm/AR40 A 80 nm) over 12 inch silicon wafers and softbaked. The coated wafer is exposed on ASML ArF 1900i with NA=1.35, Dipole 35Y illumination (0.988/0.896sigma), plus x polarization, and then post-exposure baked (PEB). The coated wafers are then treated with 0.26N (normal) aqueous tetramethylammonium hydroxide solution to develop the imaged resist layer.

Esize was determined by the exposure doses required to provide a 1:1 resolution at the top and bottom of a 90 nm line-and-space pattern ($E_{size}$ at 90 nm L:S).

Exposure latitude (EL) was defined as a difference in exposure energy to print +/−10% of the target diameter normalized by the sizing energy.

Line Width Roughness (LWR) was determined by processing the image captured by top-down scanning electron microscopy (SEM) using a Hitachi 9380 CD-SEM, operating at an accelerating voltage of 800 volts (V), probe current of 8.0 picoamperes (pA), using 200 Kx magnification. LWR was measured over a 2 μm line length in steps of 40 nm, and reported as the average for the measured region.

LWR CD denotes the CD used for LWR measurement.
Z95 is the 95% confidence interval.
Results are set forth in the following Table 1.

TABLE 1

| Resist | Additive | Esize/ mJ/ cm$^{-2}$ | % EL | LWR CD/ nm | LWR/ nm | Z95 |
|---|---|---|---|---|---|---|
| Control | Non-ionic | 22.5 | 15.2 | 40.3 | 4.01 | 0.06 |
| A | HDTMA-CHSFAM (Ionic, surface-active cation) | 27.6 | 16.0 | 40.0 | 3.48 | 0.06 |
| B (Comparative example) | TBA-CHSFAM (Ionic, non-surface-active cation) | 24.4 | 13.9 | 41.9 | 3.81 | 0.07 |
| C | TBA-HDSA (Ionic, surface-active anion) | 19.9 | 14.1 | 39.9 | 3.67 | 0.08 |
| D (Comparative example) | TBA-CSA (Ionic, non-surface-active anion) | 22.1 | 13.5 | 41.2 | 3.85 | 0.08 |

What is claimed is:

1. A photoresist comprising:
   (a) one or more resins;
   (b) one or more acid generators; and
   (c) a compound comprising a structure of the following Formula (I):

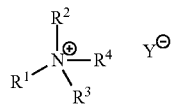

wherein in Formula (I):
   $R^1$, $R^2$ and $R^3$ are the same or different optionally substituted alkyl or heteroalkyl having 1 to 8 carbon atoms;
   $R^4$ is an optionally substituted alkyl or heteroalkyl having 10 or more carbon atoms,
   or two or more of $R^1$, $R^2$, $R^3$ and $R^4$ are taken together to form a heterocyclic or heteroaromatic ring containing the depicted nitrogen cation;
   Y is a counter anion.

2. The photoresist of claim 1 wherein $R^4$ has 10 to 30 carbon atoms.

3. The photoresist of claim 1 wherein Y in Formula (I) comprises a sulfamate moiety or a sulfonate moiety.

4. The photoresist of claim 1 wherein one or more of $R^1$, $R^2$ and $R^3$ are the same or different optionally substituted alkyl comprising 1-4 carbon atoms.

5. The photoresist of claim 1 wherein at least one of $R^1$, $R^2$, and $R^3$ comprises 1-2 carbon atoms.

6. The photoresist of claim 1 wherein Y has a pKa of between −2 and 5.

7. A photoresist comprising:
   (a) one or more resins;
   (b) one or more acid generators; and
   (c) an ionic compound comprising:
   a cationic moiety selected from:

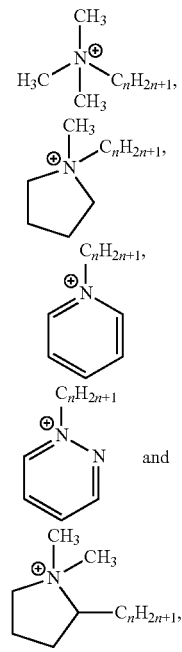

in which n is 12-18; and
an anionic moiety selected from:

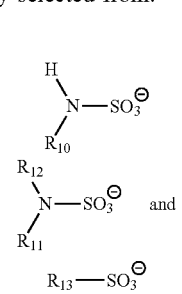

in which:
   $R_{10}$ is a linear $C_1$-$C_{18}$ alkyl group, or a cyclohexyl, adamantyl, norbornyl, or camphoryl group;
   $R_{11}$ and $R_{12}$ are each independently a linear $C_1$-$C_{18}$ alkyl group, or a cyclohexyl, adamantyl, norbornyl, or camphoryl group; and
   $R_{13}$ is a linear $C_1$-$C_{18}$ alkyl group, or a cyclohexyl, adamantyl, norbornyl, or camphoryl group.

8. A photoresist composition of claim 1 wherein $R^4$ in Formula I has 12 or more carbon atoms.

9. A photoresist of claim 1 wherein $R^4$ is not taken to form a heterocyclic or heteroaromatic ring containing the depicted nitrogen cation.

* * * * *